United States Patent [19]

Wilhelm et al.

[11] Patent Number: 4,978,359
[45] Date of Patent: Dec. 18, 1990

[54] PROSTHESIS SHAFT

[75] Inventors: Klaus Wilhelm; Johann Bauer, both of Munich; Werner Schmitt, Starnberg; Wolf-Dietrich Herold, Seefeld; Peter Koran, Weilheim; Erich Wanek; Oswald Gasser, both of Seefeld, all of Fed. Rep. of Germany

[73] Assignee: Thera Patent GmbH & Co. KG Gesellschaft fur industrielle Schutzrechte, Seefeld, Fed. Rep. of Germany

[21] Appl. No.: 343,619

[22] Filed: Apr. 27, 1989

[30] Foreign Application Priority Data

Apr. 27, 1988 [DE] Fed. Rep. of Germany ... 8805583[U]

[51] Int. Cl.$^5$ ............................................. A61F 2/32
[52] U.S. Cl. ......................................... 623/23; 623/18
[58] Field of Search ................... 623/16, 18, 20, 22, 623/23; 433/174, 175

[56] References Cited

U.S. PATENT DOCUMENTS 4,252,525 2/1981 Child ................................... 433/173
4,992,577 1/1985 Farris et al. ......................... 433/173

FOREIGN PATENT DOCUMENTS 0044915 2/1982 European Pat. Off. .
0212084 3/1987 European Pat. Off. .
2157138 5/1972 Fed. Rep. of Germany ...... 433/173
2146253 3/1973 Fed. Rep. of Germany ........ 623/18
2445758 10/1975 Fed. Rep. of Germany ........ 623/18
2461339 7/1976 Fed. Rep. of Germany .
3302968 8/1984 Fed. Rep. of Germany ...... 433/173
3445738 6/1986 Fed. Rep. of Germany .
3711884 10/1988 Fed. Rep. of Germany ...... 433/173
WO86/00011 1/1986 PCT Int'l Appl. .
1412775 7/1988 U.S.S.R. ................................ 623/22

Primary Examiner—David J. Isabella
Attorney, Agent, or Firm—Foley & Lardner, Schwartz, Jeffery, Schwaab, Mack, Blumenthal & Evans

[57] ABSTRACT

For anchoring a prosthesis within a bone by means of a bone cement (32), the prothesis shaft has a surface which is formed by the surfaces of a plurality of spheres (23 ... 25) partially penetrating each other and having radii which decrease from the proximal towards the distal shaft end. The transitional zones between adjacent spheres (23 ... 25) are concavely rounded. This shape is especially suited for use with a glass ionomer-type bone cement, because the shaft exerts substantially only compressive forces on the cement, whereas tensile and notch stresses, with respect to which this kind of cement exhibits little resistance, are largely avoided.

6 Claims, 3 Drawing Sheets

PROSTHESIS SHAFT

BACKGROUND OF THE INVENTION

This invention relates to a prosthesis shaft for the implantation of a prosthesis, especially a part of an artificial hip, knee or finger joint by means of a bone cement.

With conventional prostheses, the shaft which is to be anchored within the bone has a substantially smooth surface of conical configuration. FIGS. 1 and 2 illustrate schematically by way of a hip prosthesis the retaining forces which occur on the surface of the shaft 10 when a force P acts on the articular head 11. These retaining forces can be resolved into forces of pressure (+) and tension (−) resulting from the bonding moment of the force P multiplied by the distance e of the direction of the force from the shaft axis, and transverse or shearing forces ( ↑ ↓ ) resulting from the axial force P and acting parallel to the shaft surface. The actual load on the bone cement anchoring the shaft results from a superposition of these compressive, tensile and shearing forces.

It is known from EP-A-No. 0,212,084 to anchor a prosthesis shaft of overall conical design by means of bone cement, the shaft surface being additionally provided with cylindrical recesses.

Known bone cements are able to transmit forces of pressure and tension equally well and can also accommodate shearing forces relatively easily. But it is a significant drawback of the known bone cements that they attack the bone with the result that the life of the anchoring bond is limited and that a later re-anchoring is hardly possible because the bone is then partly destroyed.

For this reason, it has frequently been attempted to anchor prostheses in the bones without any cement. DE-A-No. 2,461,339 discloses such a prosthesis the shaft of which is substantially formed of a flat metal plate having its narrow sides provided with rounded steps within the bone. These steps are configured so that each one has an edge face directed perpendicularly to the trajectorially oriented spongiosa structure for direct transmission of the local forces of pressure and tension. The thus produced approximately sawtooth-like design of the edge faces is also intended to increase the overall area of engagement between the shaft and the bony tissue, thereby reducing the pressures acting on that area. However, the cement-free bonding attempted with such a shaft requires good growth of the bony tissue so that the sawtooth-like shaft faces are securely embedded in the required way. Even if this requirement is initially met, there will always be a risk of the cement-free anchoring to loosen in the course of time.

DE-A-No. 3,445,738 further discloses a generally hollow-cylindrical bone peg having an internal thread for receiving a bone screw and an external surface which is formed by a plurality of large spherical surfaces partially penetrating each other and being provided with axial and/or transverse slots and an additional relief, notably in the form of small spheres. This shape is intended to achieve an intimate bond with the bony tissue retained so that the cement-free anchored prosthetical part may be embedded by natural growth. Thus, a sufficient growth of the bone is again a prerequisite, and there is still the risk of the prosthetical part loosening later on.

Recently, it has been considered to use glass ionomers as bone cements, since glass ionomers are bio-inert and will thus, contrary to the conventional cements, not affect the bony tissue. Though glass ionomer-type bone cements exhibit very good compressive strength, they have little tensile strength and exhibit significant brittle fracture behaviour.

Summary of the Invention

It is an object of the present invention to provide a prosthesis shaft which may be securely and permanently anchored within the bone by the use of a glass ionomer-type bone cement.

In view of this object, the prosthesis shaft of this invention is formed as a massive body and has an outer surface formed by the surfaces of a plurality of spheres partially intersecting each other and transitional zones between respective adjacent spherical surfaces being concavely rounded. Thus, the shaft surface is configured in such a way that it is exposed substantially only to pressure, and tensile forces are substantially avoided. At the same time, edges and corners, which might lead to notch stresses and consequently to brittle fractures of the bone cement, are avoided.

Further features of the invention relate to a highly reliable interlocking anchoring and to avoiding such zones where tensile or notch stresses could occur.

BRIEF DESCRIPTION OF THE FIGURES

Embodiments of the invention will be described in detail below with reference to the remaining drawings, in which.

DETAILED DESCRIPTION OF THE PREFERRED EMBODIMENTS

Figure 1:
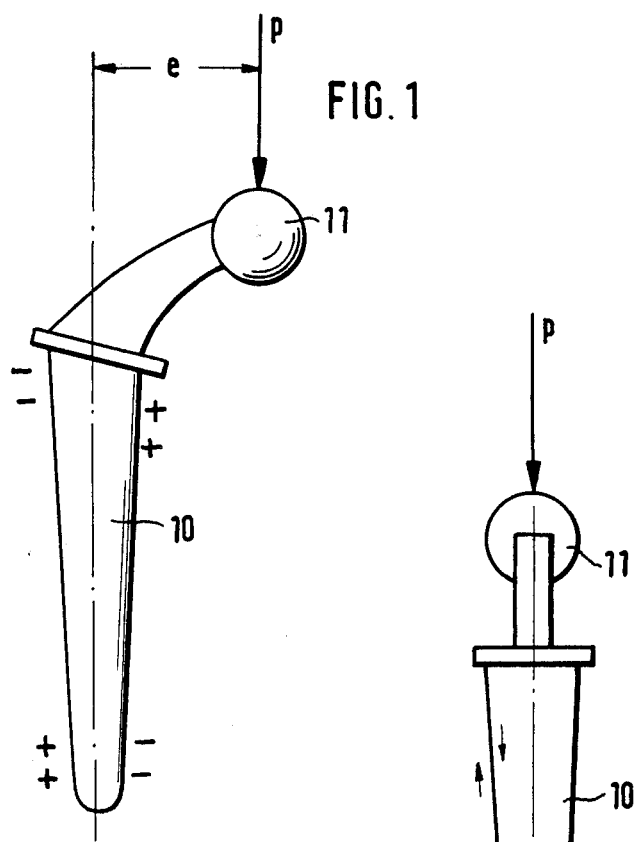
FIGS. 1 and 2 illustrate schematically, in connection with a hip prosthesis, the retaining forces produced.
Figure 2:
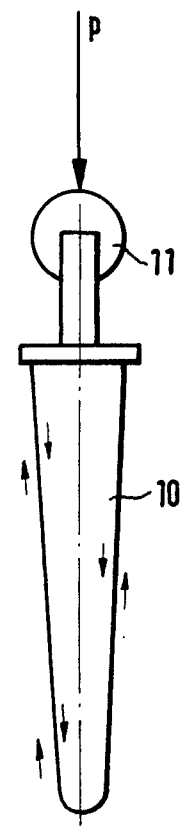
Figures 3, 4:
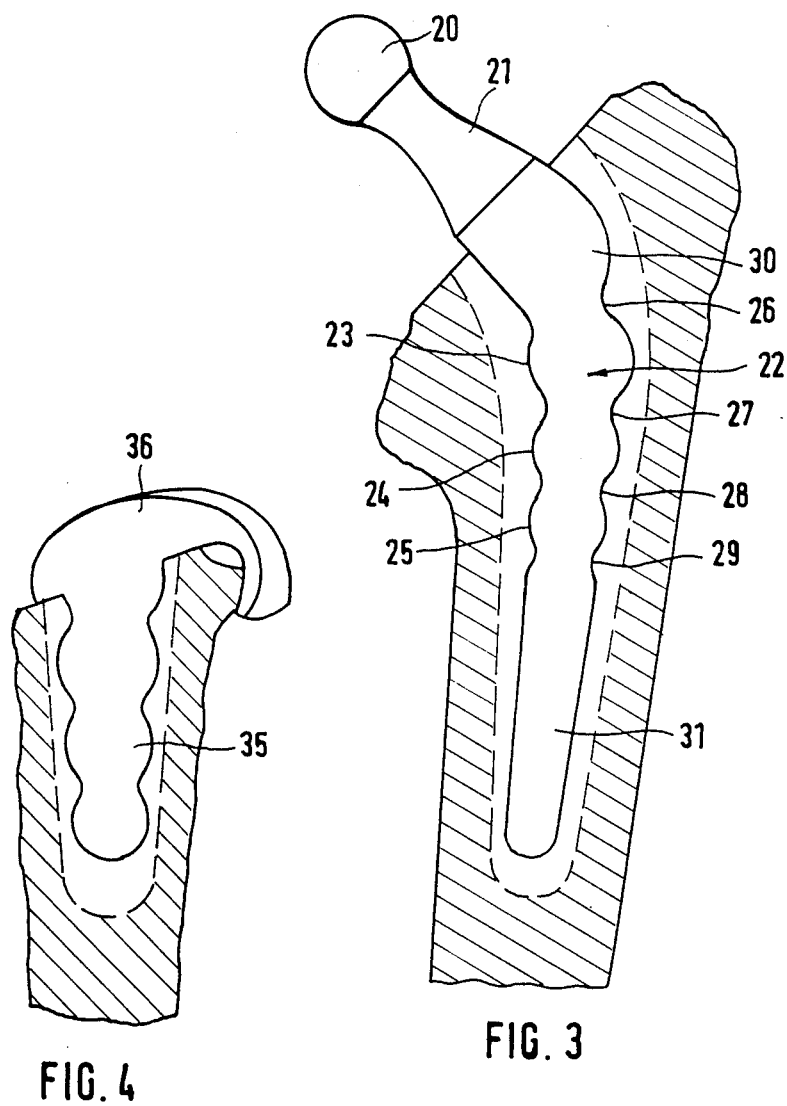
FIG. 3 shows a hip-joint prosthesis.
FIG. 4 shows a finger-joint prosthesis.

FIG. 3 shows a metallic hip-joint prosthesis having an articular head 20 joined by means of a leg 21 to a shaft generally indicated at 22. The articular head 20, the leg 21 and the shaft 22 may be formed integrally or may be assembled, for instance by screwing, from individual parts.

The upper portion of the shaft surface is composed of plural spherical surfaces 23, 24, 25 intersecting each other. The transition zones 26, 27, 28, 29 between the individual spherical surfaces 23 . . . 25, between the uppermost spherical surface 23 and the proximal shaft portion 30 joined to the leg 21, and between the lowermost spherical surface 25 and the slightly conically shaped distal shaft portion 31 are designed as concavely rounded annular surfaces.

The shape of the shaft is based on the finding that when a sphere is pressed into a viscous material only radial compressive forces will occur. This holds even if several such spheres are arranged in series along the shaft axis. As indicated by the symbols (+) in the schematic illustration of FIG. 5, with such an arrangement of a plurality of spheres, only compressive forces will occur at practically all locations in the bone cement 32. When the force P shown in FIG. 5 acts on the articular ball 20, the lower half of each sphere of the shaft will exclusively produce forces of pressure. Furthermore, each upper sphere bears on the adjacent lower sphere via the bone cement 32 so that compressive forces will exist also in the region between the spheres.

Figures 5, 6:
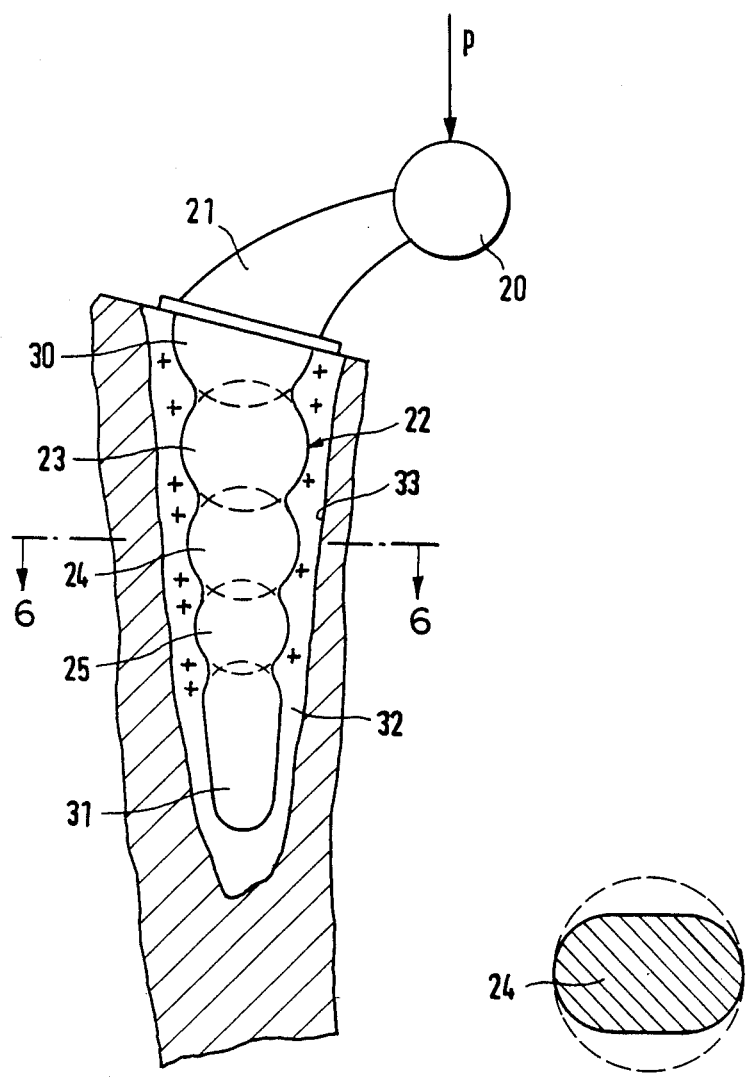
FIG. 5 is a schematic illustration similar to FIG. 3.
FIG. 6 is a sectional view taken along the line A—A of FIG. 5.

As is furthermore apparent from the schematic illustration of FIG. 5, the spheres or spherical surfaces 23 . . . 25 have radii which decrease from the proximal to the distal shaft end, and they intersect each other only to such an extent that the centres of adjacent spheres are outside the intersecting zone. Moreover it is preferable for each sphere to have a maximum radius as far as this is permitted by the cavity 33 available within the bone. This cavity 33 is constituted substantially by the natural cavity from which the marrow has been removed. The inner surface of this cavity may be abraded so as to achieve an intimate bond with the bone cement 32.

In order to prevent the prosthesis from rotating about the shaft axis relative to the bone, at least one of the spheres is flattened to an ellipsoid shape or formed otherwise unsymmetrically in its cross-section as illustrated in FIG. 6. To ensure the forces introduced from the torsional moments to be reliably accommodated, this flattened body is disposed in the middle of the shaft. In this area, additional forces are most readily accommodated without the risk of fractures. As shown by the sectional line A—A, the flattened body is the central sphere 24 in the embodiment of FIG. 5.

FIG. 4 shows an example of a design of a prosthesis shaft 35 for a finger joint. The shaft 35 itself is designed substantially analogous to the shaft 22 of the hip-joint prosthesis of FIG. 3 with a corresponding reduction in size, due to the reduced bone length available and the smaller forces occurring in this case, the distal shaft portion 31 illustrated in FIG. 3 has been omitted. The proximal joint portion 36 which starts from the shaft is designed in accordance with the natural joint socket.

We claim:

1. An implantable prosthesis comprising; an elongated shaft having a center line along its length, said shaft having opposite proximal and distal ends and configured for insertion into a cavity formed in a bone, the shaft having an outer surface formed by convex surfaces of a plurality of aligned spheres, said spheres having their centers disposed substantially along the center line of the shaft, the convex surfaces of adjacent spheres partially intersecting each other to form rounded concave transitional zones between the adjacent convex surfaces, wherein the radii of the spheres decrease from the proximal end to the distal end of the shaft.

2. The prosthesis of claim 1, wherein the centers of the spheres lie along the shaft and outside of the respective transitional zones.

3. The prosthesis of claim 1, wherein at least one sphere is flattened to prevent rotation of the shaft within the cavity.

4. An implantable prosthesis comprising; an elongated shaft having a center line along its length, said shaft having opposite proximal and distal ends and configured for insertion into a cavity formed in a bone, the shaft having an outer surface formed by convex surfaces of adjacent spheres of a plurality of aligned spheres, said spheres having their centers disposed substantially along the center line of the shaft, the convex surfaces partially intersecting each other to form rounded concave transitional zones between the adjacent convex surfaces, wherein the shaft includes at least one portion of non-circular cross-section.

5. The prosthesis of claim 4, wherein the centers of the spheres lie along the shaft and outside of the respective transitional zones.

6. The prosthesis of claim 4, wherein the radii of the spheres decrease from the proximal end to the distal end of the shaft.

* * * * *